United States Patent [19]

Fischer, deceased et al.

[11] 4,021,222

[45] May 3, 1977

[54] THIOL CARBAMATES

[75] Inventors: Adolf Fischer, deceased, late of Mutterstadt, Germany, by Caecilia Emma Fischer, heiress-at-law; Hanspeter Hansen, Ludwigshafen; Wolfgang Rohr, Mannheim, both of Germany

[73] Assignee: BASF Aktiengesellschaft, Ludwigshafen (Rhine), Germany

[22] Filed: Nov. 19, 1975

[21] Appl. No.: 633,446

[30] Foreign Application Priority Data

Dec. 6, 1974 Germany .......................... 2457688

[52] U.S. Cl. .......................... 71/88; 260/239 A; 71/90; 71/92; 71/93; 71/94; 71/95

[51] Int. Cl.² .................. A01N 9/22; C07D 205/04

[58] Field of Search .................... 71/88; 260/239 A

[56] References Cited

UNITED STATES PATENTS 3,935,190   1/1976   Fischer et al. .......................... 71/88

FOREIGN PATENTS OR APPLICATIONS 2,312,045   9/1974   Germany .............................. 71/88

Primary Examiner—Joseph P. Brust
Attorney, Agent, or Firm—Johnston, Keil, Thompson & Shurtleff

[57] ABSTRACT

The new compound S-(2,3-dichloroallyl)-(2,2,4-trimethylazetidine)-1-carbothiolate, herbicides containing this compound as active ingredient, a process for controlling the growth of unwanted plants with this compound, and a process for its manufacture.

2 Claims, No Drawings

THIOL CARBAMATES

The present invention relates to the new compound S-(2,3-dichloroallyl)-(2,2,4-trimethylazetidine)-1-carbothiolate, herbicides containing this compound as active ingredient, a process for controlling the growth of unwanted plants with this compounds, and a process for its manufacture.

It is known (German Laid-Open Application DOS 2,312,045) to use carbothiolates, e.g. S-(2,3,3-trichloroallyl)-(2,2,4-trimethylazetidine)-1-carbothiolate, as herbicides. However, their herbicidal action is poor.

We have now found that the compound S(2,3-dichloroally)(2,2,4-trimethylazetidine)-1-carbothiolate of the formula

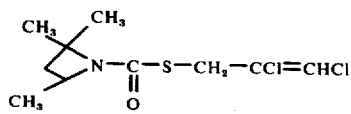

has a better herbicidal action than the abovementioned prior art compound.

The compound of the invention is prepared by reacting 2,2,4-trimethylazetidine with carbonyl sulfide and 2,3-dichloroallyl chloride in the presence of a trialkylamine. The halogen atoms of the dichloroallyl radical may be in either the cis or trans position.

EXAMPLE 1

38.6 parts (by weight) of 2,2,4-trimethylazetidine and 39.3 parts of triethylamine are added to 200 parts of dry benzene. At 0° C, 23.4 parts of COS is passed into this solution. The temperature of the mixture is then allowed to rise to room temperature, and is then stirred for a further hour. At 0° to +5° C, a solution of 57.0 parts of 2,3-dichloroallyl chloride in 100 parts of anhydrous benzene is then dripped in. Up to completion of the reaction the mixture is stirred at room temperature; the precipitated triethylamine hydrochloride is removed, and extraction is carried out with water. After drying has been effected, the solvent is evaporated and the residue distilled in vacuo. Boiling point (0.01 mm): 111°-112° C $n_D^{25}$: 1.5269

Yield: 57.0 parts of the compound of the invention.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling points, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylat polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, wetting agents or adherents, herbicides, fungicides, nematocides, insecticides, bactericides, trace elements, fertilizers, antifoams (e.g., silicones), growth regulators, antidotes and other herbicidally effective compounds such as
  substituted anilines
  substituted aryloxycarboxylic acids and salts, esters and
  amides thereof,
  substituted ethers
  substituted arsonic acids and their salts, esters and amides
  substituted benzimidazoles
  substituted benzisothiazoles
  substituted benzothiadiazinone dioxides
  substituted benzoxazines substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substitutes piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
etc.;
Cyperaceae, such as
Carex spp.
Cyperus spp.
etc.;
dicotyledonous weeds, such as
Malvaceae, e.g.
Abutilon theoprasti
Sida spp.
etc.;
Compositae, such as
Ambrosia spp.
Lactuca spp.
Senecio spp.

Dactylis spp.
Avena spp.
Bromus spp.
Uniola spp.
Poa spp.
Leptochloa spp.
Brachiaria spp.
Eleusine spp.
Cenchrus spp.
Eragrostis spp.
Phragmites communis Eleocharis spp.
Scirpus spp.

Hibiscus spp.
Malva spp.

Centaurea spp.
Tussilago spp.
Lapsana communis

-continued

Sonchus spp.
Xanthium spp.
Iva spp.
Galinsoga spp.
Taraxacum spp.
Chrysanthemum spp.
Cirsium spp.
Convolvulaceae, such as
Convolvulus spp.
Ipomoea spp.
etc.;
Cruciferae, such as
Barbarea vulgaris
Brassica spp.
Capsella spp.
Sisymbrium spp.
Thlaspi spp.
Sinapis arvensis
etc.;
Geraniaceae, such as
Erodium spp.
etc.;
Portulacaceae, such as
Portulaca spp.
Primalaceae, such as
Anagallis arvensis
etc.;
Rubiaceae, such as
Richardia spp.
Galium spp.
Scrophulariacea, such as
Linaria spp.
Veronica spp.
Solanaceae, such as
Physalis spp.
Solanum spp.
etc.;
Urticaceae, such as
Urtica spp.
Violaceae, such as
Viola spp.
Zygophyllaceae, such as
Tribulus terrestris
Euphorbiaceae, such as
Mercurialis annua
Umbelliferae, such as
Daucus carota
Aethusa cynapium
Chenopodiaceae, such as
Chenopodium spp.
Kochia spp.
Salsola Kali
Lythraceae, such as
Cuphea spp.
Oxalidaceae, such as
Oxalis spp.
Ranunculaceae, such as
Ranunculus spp.
Delphinium spp.
Papaveraceae, such as
Papaver spp.
etc.;
Onagraceae, such as
Jussiacea spp.
Rosaceae, such as
Alchemillia spp.
etc.;
Potamogetonaceae, such as
Potamogeton spp.
Najadaceae, such as
Najas spp.
Equisetaceae
Equisetum spp.
Marsileaceae, such as
Marsilea quadrifolia
Polypodiaceae,
Pteridium quilinum
Alismataceae, such as
Alisma spp.
etc.

Tagetes spp.
Erigeron spp.
Anthemis spp.
Matricaria spp.
Artemisia spp.
Bidens spp.
etc.;

Cuscuta spp.
Jaquemontia tamnifolia

Arabidopsis thaliana
Descurainia spp.
Draba spp.
Coronopus didymus
Lepidium spp.
Raphanus spp.

Geranium spp.

etc.;

Lysimachia spp.

Diodia spp.
etc.;

Digitalis spp.
etc.;

Nicandra spp.
Datura spp.

etc.;

etc.;

Euphorbia spp.

Ammi majus
etc.;

Atriplex spp.
Monolepsis nuttalliana
etc.;

etc.;

etc.;

Adonis spp.
etc.;

Fumaria offinicalis etc.;

Potentilla spp.

etc.;

etc.;

etc.;

etc.;

Sagittaria sagittifolia

The herbicides according to the invention may be employed in cereal crops such as
Avena spp.
Triticum spp.
Hordeum spp.
Secale spp.
Saccharum offinicarum
and in dicotyledon crops such as
Cruciferae, e.g.
Brassica spp.
Sinapis spp.
Compositae, e.g.
Lactuca spp.

Sorghum
Zea mays
Panicum miliaceum
Oryza spp.

Raphanus spp.
Lepidium spp.

Carthamus spp.

-continued

Helianthus spp.
Malvaceae, e.g.
Gossypium hirsutum
Leguminosae, e.g.
Medicago ssp.
Trifolium spp.
Pisum spp.
Chenopodiaceae, e.g.
Beta vulgaris
Spinacia spp.
Solanaceae, e.g.
Solanum spp.
Nicotiania spp.
Linaceae, e.g.
Linum spp.
Umbelliferae, e.g.
Petroselinum spp.
Daucus carota
Rosaceae, e.g.
Cucurbitaceae, e.g.
Cucumis spp.
Liliaceae, e.g.
Allium spp.
Vitaceae, e.g.
Vitis vinifera
Bromeliaceae, e.g.
Ananas sativus.

Scorzonera spp.

Phaseolus spp.
Arachis spp.
Glycine max.

Capsicum annuum

Apium graveolens

Fragaria

Cucurbita spp.

EXAMPLE 2

In the greenhouse, loamy sandy soil was filled into pots and sown with various seeds. The solid prepared in this manner was then immediately treated with I S-(2,3-dichloroallyl)-(2,2,4-trimethylazetidine)-1-carbothiolate and, for comparison, II S-(2,3,3-trichloroallyl)-(2,2,4-trimethylazetidine)-1-carbothiolate.

The application rates for both compounds were 0.8 and 1.6 kg/ha, each amount being dispersd or emulsified in 500 liters of water per hectare.

After 3 to 4 weeks it was ascertained that active ingredient I had a better herbicidal action that active ingredient II, combined with the same crop plant compatibility.

The results are given below:

| Active ingredient kg/ha | I | | II | |
|---|---|---|---|---|
| | 0.8 | 1.6 | 0.8 | 1.6 |
| Crop plants: | | | | |
| Beta vulgaris | 0 | 0 | 0 | 0 |
| Beta vulgaris var. conditiva | 0 | 0 | 0 | 0 |
| Beta vulgaris var. altissima | 0 | 0 | 0 | 0 |
| Triticum aestivum | 0 | 0 | 0 | 0 |
| Hordeum vulgare | 0 | 0 | 0 | 0 |
| Secale cereale | 0 | 0 | 0 | 25 |
| Brassica napus | 0 | 0 | 0 | 0 |
| Unwanted plants: | | | | |
| Alopecurus myosuroides | 95 | 100 | 75 | 95 |
| Avena sterilis | 75 | 95 | 30 | 80 |
| Avena fatua | 80 | 100 | 35 | 85 |
| Lolium multiflorum | 90 | 100 | 70 | 90 |
| Poa annua | 95 | 100 | 75 | 95 |
| 0 = no damage | | | | |
| 100 = complete destruction | | | | |

EXAMPLE 3

In the greenhouse, various plants were treated at a growth height of from 2 to 20 cm with 0.8 kg/ha of each of the following active ingredient, each being dispersed or emulsified in 500 liters of water per hectare:

I S-(2,3-dichloroallyl)-(2,2,4-trimethylazetidine)-1-carbothiolate and, for comparison II S-(2,3,3-trichloroallyl)-(2,2,4-trimethylazetidine)-1-carbothiolate.

After 2 to 3 weeks it was ascertained that active ingredient I had a better herbicidal action than II, combined with the same crop plant compatibility.

The results are given below:

| Active ingredient kg/ha | I 0.8 | II 0.8 |
|---|---|---|
| Crop plants: | | |
| Beta vulgaris | 0 | 0 |
| Triticum aestivum | 0 | 0 |
| Unwanted plants: | | |
| Alopecurus myosuroides | 80 | 60 |
| Avena fatua | 70 | 35 |
| Lolium multiflorum | 80 | 60 |
| 0 = no damage | | |
| 100 = complete destruction | | |

I S-(2,3-dichloroallyl)-(2,2,4-trimethylazetidine)-1-carbothiolate
  each at rates of 0.25, 0.5, 0.75, 1, 1.5, 2, 3 and 4 kg/ha;
IV + I and III + I
  each at rates of 0.25 + 0.75, 0.75 + 0.25, 2 + 1, 1 + 2, 1.5 + 1.5 and 2 + 2 kg/ha;
IV + I + III
  at rates of 0.25 + 0.25 + 0.5, 0.25 + 0.5 + 0.25, 0.5 + 0.25 + 0.25, 0.25 + 0.25 + 1.5, 0.25 + 1.5 + 0.25 and 1.5 + 0.25 + 0.25 kg/ha.

After 4 to 5 weeks it was ascertained that at the lower application rates the compositions had a better herbicidal action than their components and the same crop plant compatibility, and at the higher application rates the compositions had better crop plant compatibility than their components.

The results are given below:

| Active ingredient kg/ha | IV | | | | | | | |
|---|---|---|---|---|---|---|---|---|
| | 0.25 | 0.5 | 0.75 | 1 | 1.5 | 2 | 3 | 4 |
| Crop plants: | | | | | | | | |
| Beta vulgaris | 0 | 0 | 0 | 0 | 0 | 0 | 0 | 10 |
| Unwanted plants: | | | | | | | | |
| Avena fatua | 0 | 5 | 8 | 12 | 15 | 20 | 40 | 75 |
| Echinochloa crus-galli | 5 | 6 | 10 | 13 | 20 | 32 | 65 | 75 |
| Matricaria chamomilla | 15 | 20 | 30 | 40 | 60 | 85 | 100 | 100 |
| Active ingredient | III | | | | | | | |
| Beta vulgaris | 0 | 0 | 0 | 0 | 0 | 0 | 0 | 10 |
| Avena fatua | 10 | 15 | 30 | 40 | 45 | 54 | 75 | 80 |
| Echinochloa crus-galli | 20 | 25 | 45 | 70 | 90 | 100 | 100 | 100 |
| Matricaria chamomilla | 5 | 15 | 25 | 35 | 55 | 80 | 90 | 95 |
| Active ingredient | I | | | | | | | |
| Beta vulgaris | 0 | 0 | 0 | 0 | 10 | 5 | 10 | 15 |
| Avena fatua | 20 | 40 | 80 | 90 | 95 | 98 | 100 | 100 |
| Echinochloa crus-galli | 5 | 10 | 15 | 20 | 30 | 40 | 45 | 50 |
| Matricaria chamomilla | 0 | 2 | 5 | 8 | 10 | 15 | 20 | 30 |

| Active ingredient kg/ha | IV + I | | | | | |
|---|---|---|---|---|---|---|
| | 0.25+0.75 | 0.75+0.25 | 2+1 | 1+2 | 1.5+1.5 | 2+2 |
| Beta vulgaris | 0 | 0 | 0 | 5 | 0 | 5 |
| Avena fatua | 100 | 95 | 100 | 100 | 100 | 100 |
| Echinochloa crus-galli | 60 | 55 | 90 | 92 | 90 | 100 |
| Matricaria chamomilla | 60 | 70 | 100 | 100 | 100 | 100 |
| Active ingredient kg/ha | III + I | | | | | |
| | 0.25+0.75 | 0.75+0.25 | 2+1 | 1+2 | 1.5+1.5 | 2+2 |
| Beta vulgaris | 0 | 0 | 0 | 5 | 0 | 5 |
| Avena fatua | 100 | 100 | 100 | 100 | 100 | 100 |
| Echinochloa crus-galli | 75 | 90 | 100 | 100 | 100 | 100 |
| Matricaria chamomilla | 50 | 65 | 100 | 100 | 100 | 100 |
| Active ingredient kg/ha | IV + III + I | | | | | |
| | 0.25+0.25+0.5 | 0.25+0.5+0.25 | 0.5+0.25+0.25 | 0.25+0.25+1.5 | 0.25+1.5+0.25 | 1.5+0.25+0.25 |
| Beta vulgaris | 0 | 0 | 0 | 0 | 0 | 0 |
| Avena fatua | 95 | 95 | 97 | 100 | 100 | 100 |
| Echinochloa crus-galli | 73 | 75 | 78 | 100 | 100 | 100 |
| Matricaria chamomilla | 60 | 70 | 62 | 90 | 100 | 100 |

0 = no damage
100 = complete destruction

EXAMPLE 4

In the greenhouse, loamy sandy soil was filled into pots and sown with the seeds of various plants. Subsequently, the soil prepared in this manner was treated with the following amounts of the following individual active ingredients and compositions thereof as dispersions or emulsions:

IV 1-phenyl-4-amino-5-chloropyridazone-(6)

III O-(methylaminosulfonyl)-glycolic acid-N-isopropylanilide

EXAMPLE 5

In the greenhouse, loamy sandy soil was filled into pots and sown separately, according to species, with the seeds of various plants. The soil prepared in this manner was then immediately treated with I S-(2,3-dichloroallyl)-(2,2,4-trimethylazetidine)-1-carbothiolate II 2,3-dichloroallyl N,N-diisopropylthiolcarbamate III 2,2,3-trichloroallyl N,N-diisopropylthiolcarbamate, each amount of each substance being emulsified in 500 liters of water per hectare. After the soil had been sprayed, each pot was watered and covered with a transparent plastic hood. This hood was only removed after the plants had emerged. During the experiment the pots were kept moist.

The plants employed, the active ingredient concentrations and the results obtained are given in the following table.

Active ingredient I is superior to comparative compound III in its action on unwanted grasses. The compatibility of I with cereals is far better than that of II.

| Active ingredient kg/ha | I | | | II | | | III | | |
|---|---|---|---|---|---|---|---|---|---|
| | 0.4–0.5 | 0.8–1.0 | 1.5–2.0 | 0.4–0.5 | 0.8–1.0 | 1.5–2.0 | 0.4–0.5 | 0.8–1.0 | 1.5–2.0 |
| Beta vulgaris | 0 | 0 | 6 | 0 | 0 | 0 | 0 | 0 | 0 |
| Hordeum vulgare | 0 | 0 | 0 | 0 | 40 | 60 | 0 | 0 | 0 |
| Secale cereale | 0 | 0 | 0 | 20 | 40 | 80 | 0 | 20 | 40 |
| Triticum aestivum | 13 | 23 | 40 | 47 | 63 | 75 | 47 | 47 | 80 |
| Alopecurus myosuroides | 66 | 86 | 96 | 36 | 61 | 95 | 0 | 57 | 70 |
| Avena fatua | 80 | 88 | 95 | 62 | 85 | 95 | 50 | 81 | 95 |
| Bromus inermis | 100 | 100 | — | 90 | 95 | — | 40 | 95 | — |
| Digitaria sanguinalis | 60 | 90 | — | 60 | 90 | — | 0 | 10 | — |
| Eleusine indica | 90 | 95 | — | 50 | 95 | — | 40 | 90 | — |
| Sorghum halepense | 20 | 70 | — | 10 | 45 | — | 5 | 55 | — |

0 = no damage
100 = complete destruction

EXAMPLE 6

In the open, separate experiments - depending on the crop plants used — were carried out with the following active ingredients:

I S-(2,3-dichloroallyl)-(2,2,4-trimethylazetidine)-1-carbothiolate
II 2,3-dichloroallyl N,N-diisopropylthiolcarbamate
III 2,2,3-trichloroallyl N,N-diisopropylthiolcarbamate each amount of each compound being emulsified in 700 liters of water per hectare. The soil, which had been prepared for sowing, was sprayed and cultivated to a depth of 5 cm within an hour to incorporate the active ingredients into the soil. Sowing followed. The soil was a sandy loam. Rainfall was normal.

The following table contains the test plants, the active ingredient application rates, and the results.

1. The average action of all three compounds on Alopecurus myosuroides and Avena fatua is unexpectedly poor.
2. Active ingredient I is superior to III in its action on Alopecurus myosuroides and to II in its compatibility with barley and wheat.

EXAMPLE 7

90 parts by weight of compound I is mixed with 10 parts by weight of N-methyl-α-pyrrolidone. A mixture is obtained which is suitable for application in the form of very fine drops.

EXAMPLE 8

20 parts by weight of compound I is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the soluton into 100,000 parts by weight of water and uniformly distributing it therein, an aqueous dispersion is obtained containing 0.02% by weight of the active ingredient.

EXAMPLE 9

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

| Active ingredient kg/ha | I | | | II | | | III | | |
|---|---|---|---|---|---|---|---|---|---|
| | 1.0 | 1.5 | 2.0 | 1.0 | 1.5 | 2.0 | 1.0 | 1.5 | 2.0 |
| Beta vulgaris | 0 | 0 | 0 | — | 0 | 0 | 0 | 0 | 0 |
| Hordeum vulgare | 0 | 0 | 0 | 0 | 5 | 2.5 | 0 | 0 | 0 |
| Triticum aestivum | 10 | 15 | 15 | 20 | 30 | 35 | 0 | 0 | 0 |
| Alopecurus myosuroides | 68 | 67 | 81 | 53 | 66 | 87 | 41 | 50 | 63 |
| Avena fatua | 48 | 61 | 65 | 47 | 57 | 85 | 41 | 52 | 68 |

0 = no damage
100 = complete destruction

EXAMPLE 11

20 parts by weight of compound I is well mixed with 3 parts by weight of the sodium salt of diisobutylnaphthalene- -sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound I is intimately mixed with 97 parts by weight of particulate kaolin. A dust is obtained containing 3% by weight of the active ingredient.

EXAMPLE 13

30 parts by weight of compound I is intimately mixed with a mixture consisting of 92 parts by weight of powdered silica gel and 8 parts by weight of paraffin oil which has been sprayed onto the surface of this silical gel. A formulation of the active ingredient is obtained having good adherence.

We claim:
1. S-(2,3-dichloroallyl)-(2,2,4-trimethylazetidine)-1-carbothiolate.
2. A process for controlling the growth of unwanted plants wherein the soil or the plants are treated with a herbicidally effective amount of S-(2,3-dichloroallyl)-(2,2,4-trimethylazetidine)-1-carbothiolate.

* * * * *